(12) United States Patent
O'Neil et al.

(10) Patent No.: US 9,044,286 B2
(45) Date of Patent: Jun. 2, 2015

(54) ENHANCED SURGICAL DRIVER (71) Applicant: DePuy Synthes Products, Inc., Raynham, MA (US)

(72) Inventors: Michael O'Neil, West Barnstable, MA (US); Andrew Topulous, Wareham, MA (US); Robert Hurley, Carver, MA (US)

(73) Assignee: DePuy Synthes Products, Inc.

( * ) Notice: Subject to any disclaimer, the term of this patent is extended or adjusted under 35 U.S.C. 154(b) by 235 days.

(21) Appl. No.: 13/668,892

(22) Filed: Nov. 5, 2012

(65) Prior Publication Data
US 2014/0128878 A1    May 8, 2014

(51) Int. Cl.
| A61B 17/58 | (2006.01) |
| A61B 17/60 | (2006.01) |
| A61F 2/00 | (2006.01) |
| A61B 17/88 | (2006.01) |
| B25B 23/14 | (2006.01) |
| B25B 23/142 | (2006.01) |
| A61B 19/00 | (2006.01) |

(52) U.S. Cl.
CPC ......... *A61B 17/8875* (2013.01); *B25B 23/1415* (2013.01); *B25B 23/1427* (2013.01); *A61B 2019/301* (2013.01)

(58) Field of Classification Search
USPC ........................................... 606/104, 99, 916
See application file for complete search history.

(56) References Cited

U.S. PATENT DOCUMENTS

| 4,215,600 A | 8/1980 | Kesselman |
| 4,420,281 A | 12/1983 | Dehoff |
| 4,838,264 A | 6/1989 | Bremer et al. |
| 5,158,458 A | 10/1992 | Perry |
| 5,176,050 A | 1/1993 | Sauer et al. |
| 5,295,831 A | 3/1994 | Patterson et al. |
| 5,299,474 A | 4/1994 | Hohmann et al. |
| 5,347,894 A | 9/1994 | Fischer |
| 5,368,480 A | 11/1994 | Balfour et al. |
| 5,735,668 A | 4/1998 | Klein |
| 5,868,047 A | 2/1999 | Faust et al. |
| 5,941,885 A | 8/1999 | Jackson |
| 5,964,011 A | 10/1999 | Ruston et al. |
| 6,056,753 A | 5/2000 | Jackson |
| 6,059,786 A | 5/2000 | Jackson |

(Continued)

OTHER PUBLICATIONS

[No author listed] CD Horizon Legacy 5.5 Spinal System—Degenerative Surgical Technique. Medtronic Sofamor Danek. 38 pages. 2004.

(Continued)

*Primary Examiner* — Sameh Boles
(74) *Attorney, Agent, or Firm* — Nutter McClennen & Fish LLP (57) ABSTRACT

Devices, systems, and methods are provided for applying a controlled amount of torque during a surgical procedure. In one exemplary embodiment, after the amount of torque applied reaches a threshold amount, a modular driver tip can be deformed, for instance by breaking into pieces. A containment shield disposed around at least a portion of the tip is configured to receive at least a portion of the tip after it is deformed. In one aspect, multiple modular driver tips can be disposed in a cartridge, with a distal-most tip being held by a driver tip holder that has a holding force that is greater than a threshold torque value of the tip. Exemplary methods for operating surgical drivers and systems that include tips that deform at a threshold torque value, and a multitude of embodiments of tools and systems, are also provided.

11 Claims, 8 Drawing Sheets

(56) References Cited

U.S. PATENT DOCUMENTS

| | | | |
|---|---|---|---|
| 6,102,913 A | 8/2000 | Jackson | |
| 6,179,841 B1 | 1/2001 | Jackson | |
| 6,224,598 B1 | 5/2001 | Jackson | |
| 6,308,598 B1 * | 10/2001 | O'Neil | 81/467 |
| 6,606,924 B2 | 8/2003 | Chandler et al. | |
| 6,884,244 B1 | 4/2005 | Jackson | |
| 7,127,955 B2 | 10/2006 | Bondhus et al. | |
| 7,144,252 B2 | 12/2006 | Walton | |
| 7,159,494 B2 | 1/2007 | Jamnia et al. | |
| 7,188,556 B1 * | 3/2007 | Rinner | 81/467 |
| 7,243,580 B2 | 7/2007 | Frazee | |
| 7,299,725 B2 | 11/2007 | Helstern et al. | |
| 7,331,263 B2 | 2/2008 | Erickson et al. | |
| D623,036 S | 9/2010 | DeBaker | |
| D631,723 S | 2/2011 | DeBaker | |
| D646,547 S | 10/2011 | Debaker | |
| 8,028,608 B2 | 10/2011 | Sixto, Jr. et al. | |
| D658,465 S | 5/2012 | Hsu | |
| D662,802 S | 7/2012 | DeBaker | |
| D663,186 S | 7/2012 | Hsu | |
| D663,187 S | 7/2012 | DeBaker | |

OTHER PUBLICATIONS

[No author listed] CD Horizon Legacy 5.5 Spinal System. Medtronic Sofamor Danek. 5 pages. 2003.

[No author listed] CD Horizon Legacy Reduction Multi Axial Screw. Spinal System Surgical Technique. Medtronic Sofamor Danek. 8 pages. 2005.

[No author listed] CD Horizon Solera Spinal System. Product Overview. Medtronic. 16 pages. 2010.

[No author listed] CD Horizon Solera Spinal System. Surgical Technique. Medtronic. Product Overview. 72 pages. 2010.

* cited by examiner

ENHANCED SURGICAL DRIVER

FIELD

The present disclosure relates to devices, systems, and methods to facilitate the application of a desired level of torque to an implantable component during a medical procedure, and more particularly to devices, systems, and methods for recovering modular tips used to apply the desired torque to the implantable component after the desired level of torque has been applied.

BACKGROUND

Some surgical procedures, such as those involving installation of a joint prosthesis, rely on the use of components that must be securely attached to other components, such as a prosthetic device or to bony anatomy. If, in attaching a component, the component is either oversecured or undersecured, there can be associated negative effects. For example, an undersecured component may loosen, while an oversecured component may impart an undesirable amount of stress to one or both of the components, including component fracture and/or striping of the drive feature or threaded attachment.

Normally, the attachment of an implant component to another implant component and/or to a prosthetic device is done using devices and methods that impart assembly torque throughout the attachment process. A certain level of torque is required to properly secure a component, sometimes referred to as a driven member. To assist operators in being able to perceive when the proper level of torque has been imparted on the driven member, devices have been developed to help ensure that a consistent and/or limited amount of torque is imparted on the driven member to properly secure torque-applied components to other components or bony anatomy. Among these devices are torque-limiting drivers that are calibrated to impart a desired level of torque to a component during the attachment of the component to another component such as a prosthetic device.

Torque limiting drivers, however, can suffer from some notable complications. For example, driver tip failures are the subject of frequent complaints, as documented in the U.S. Food and Drug Administration (FDA) Manufacturer and User Facility Device Experience (MAUDE) database. Driver tip failures can result in an insufficient or excessive amount of torque being applied, and can also lead to unplanned implantation of the driver tip in the body after failure has occurred. For example, if a driver tip or breakaway implant is configured to fail by fracturing after a desired torque level is achieved, the rough surfaces at the fracture can cause undesirable harm to tissue at the surgical site, or elsewhere in the body if the tip is not retrieved. Additionally, if the portion of the fractured tip is left engaged with the driven member, additional torque cannot be applied to the driven member because the fractured tip prevents engagement by a new driver tip. If a driver tip fails and it is retrieved, such retrieval is typically done manually. Likewise, if a new tip is required for further torque application, it is also typically attached manually. This can lead to the driver being frequently inserted and removed from the body, thereby increasing the risk of infections and other complications. Still further, existing torque limiting drivers can also have inconsistencies following manufacturing, reuse, cleaning, and reprocessing. New more aggressive cleaning materials and requirements can decrease the cost effectiveness and reliability of a reusable torque limiting driver.

It is therefore desirable to provided devices, systems, and methods that improve the consistency and reliability of torque limiting drivers and reduce the risks associated with driver tip failures.

SUMMARY

Devices, systems, and methods are generally provided for applying torque to a component during a surgical procedure. In one exemplary embodiment a surgical tool includes a driver, a modular driver tip, and a containment shield disposed around at least a portion of the modular driver tip. The driver can have a proximal handle, a distal end, and a shaft disposed therebetween. The modular driver tip can have a proximal end that is removably and replaceably matable to the distal end of the driver and a distal end that is configured to apply torque from the driver to a driven member. The tip can be configured to deform at a threshold torque value applied by the driver. In some embodiments the deformation of the tip can result in the tip breaking into two or more pieces. The containment shield can receive at least a portion of the modular driver tip after tip deformation occurs.

The containment shield can be configured to be removable from a surgical site. As a result, the portion of the modular driver tip that is received by the containment shield can also be removed from the surgical site. In some embodiments the containment shield can be press fit around at least a portion of the modular driver tip, while in some other embodiments the containment shield can be heat shrunk around at least a portion of the modular driver tip. The containment shield can be fixedly coupled to at least one of a proximal portion and a distal portion of the modular driver tip. Further, in some embodiments the containment shield can be freely rotatable with respect to the shaft of the driver. The container shield can include a container that is configured to retain the portion of the modular driver tip after its deformation. In some embodiments the containment shield can include one or more elastic materials.

A system of modular driver tips can include more than one modular driver tip. Each tip can have a proximal end that is removably and replaceably matable to the distal end of the driver and a distal end that is configured to apply torque from the driver to a driven member. Further, each tip can be configured to deform at a threshold torque value applied by the driver, and each tip can have a containment shield disposed around at least a portion of the tip to receive at least a portion of the respective modular driver tip after deformation occurs. In some embodiments, each modular driver tip can include a threshold designation marker indicative of the threshold torque value at which the modular driver tip deforms. For example, the threshold designation marker can be a color, and different colors can designate different threshold torque values.

In one exemplary embodiment of a surgical tool system, the system includes a handle, a plurality of modular driver tips disposed within an interior volume of a cartridge assembly, and a driver tip holder that is distal to the handle and is in communication with the interior volume of the cartridge. Each modular driver tip can be configured to deform at a predetermined threshold torque value. For example, the modular driver tips can be configured to break into two or more pieces at a torque that is greater than the threshold torque value. A containment shield can be disposed around at least a portion of at least one of the modular driver tips. The shield can receive at least a portion of the modular driver tip after it deforms. The driver tip holder can be configured to engage one of the modular driver tips, or a shield associated therewith, with a holding force such that the modular driver tip is capable of applying torque to a driven member. The holding force supplied by the driver tip holder is greater than the threshold torque value. In some embodiments the holding force can be greater than or equal to two times the threshold torque value.

An alignment feature can be disposed within the cartridge. The alignment feature can be configured to align a modular driver tip that is proximally adjacent to the driver tip holder with the driver tip holder. This readies the proximally adjacent tip for insertion into the driver tip holder once any previously deformed tip is removed from the holder. In some embodiments the modular driver tips can be cannulated, and the system can include a guide wire disposed through at least a portion of the cartridge and extending through each of the plurality of modular driver tips. In some other embodiments the cartridge can include a rotatable, multiple chamber cylinder. Each chamber can have a modular driver tip disposed therein, and the cylinder can be configured to rotate to place each chamber in line with the driver tip holder so that the modular driver tip disposed in the chamber that is in line with the driver tip holder can be seated in the driver tip holder. In still other embodiments the cartridge can include a first sleeve and the driver tip holder can include a second sleeve that is at least partially disposed in the first sleeve. The first and second sleeves can be movable relative to each other to move a modular driver tip from the cartridge and into engagement with the driver tip holder.

In another exemplary embodiment of a surgical tool, the tool includes a handle having at least one breakaway member, a receiver having at least one torque-limiting feature, and a driver tip disposed distal of the receiver and configured to apply torque from the handle to a driven member. The torque-limiting feature of the receiver can be configured to shear the at least one breakaway member of the handle when a threshold torque value is exceeded. When the breakaway member is sheared, the driver tip can no longer apply torque to the driven member. In some embodiments the receiver can be a cartridge having a proximal end in which the torque-limiting feature is located and a distal end configured to mate with the driver tip. The torque-limiting feature can be, for example, at least one bore for receiving that at least one breakaway member. The at least one breakaway member can sometimes be a plurality of depressible keys and the at least one bore can be a plurality of bores. In such embodiments, each key can be configured to become disposed in one bore of the plurality of bores at individually designated threshold torque values such that the key is sheared within the respective bore when the individually designated threshold torque value is exceeded for that key and bore combination. In some other embodiments the receiver can be a shear ring. The shear ring can be coupled to a proximal end of a shaft, and the shaft can have a distal end that is coupled to the driver tip. The torque-limiting feature can be, for example, a webbing. In such embodiments, the breakaway member can travel through the webbing until the threshold torque value is exceeded, at which point the breakaway member is sheared by the webbing.

In one exemplary embodiment a surgical method includes operating a surgical driver to apply torque to a driven member through a modular driver tip attached to the surgical driver, applying torque to the driven member until a threshold torque value is attained such that the modular driver tip deforms at the threshold torque value and is unable to apply an amount of torque greater than the threshold torque value, and maintaining the deformed modular driver tip within a containment shield associated with the surgical driver. The method can also include removing the deformed modular driver tip from a surgical site and attaching a second modular driver tip to the surgical driver. Still further, the method can include inserting the modular driver tip and the driven member to a surgical site, with the driven member being coupled to the modular driver tip prior to the insertion step. In such an instance, the modular driver tip can be decoupled from the driven member after the threshold torque value is reached and removed from the surgical site.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the embodiments generally have similar features. For instance, a person skilled in the art will recognize that features of the modular driver tip of FIGS. 2A-2C, the modular driver tip of FIGS. 3A and 3B, the modular driver tip of FIGS. 4A-4C, the modular driver tip of FIGS. 5A-5C, and the modular driver tips of FIGS. 12A and 12B can be adapted interchangeably without departing from the spirit of the invention. Additionally, to the extent that linear or circular dimensions are used in the description of the disclosed devices, systems, and methods, such dimensions are not intended to limit the types of shapes that can be used in conjunction with such devices, systems, and methods. A person skilled in the art will recognize that an equivalent to such linear and circular dimensions can easily be determined for any geometric shape.

Devices, systems, and methods for applying torque to an implant component, such as a fastener, are generally provided. In particular, enhanced surgical drivers and systems are disclosed for applying torque to an implant component, referred to herein as a driven member. The drivers and systems disclosed herein each include a modular driver tip that mates with the driven member such that torque applied to the surgical driver is also applied to the modular driver tip and the driven member mated thereto. The modular driver tip is configured to deform when a torque applied to the tip reaches or exceeds a threshold value. The deformed tip can, for example, break into two or more pieces when the threshold torque value is met or exceeded, thereby preventing further torque from being applied to the tip, and thus to the driven member mated to the tip. A containment shield can be associated with the modular driver tip to receive at least a portion of the modular driver tip after it has deformed. The shield, and the portions of the tip associated therewith, can then be removed from the surgical site. Another, undeformed driver tip can then be coupled to a distal end of the surgical driver to apply torque to the same or a different driven member. The second and subsequent driver tips can, for instance, be disposed in a cartridge designed to provide tips in a sequential manner after the torque-applying tip becomes deformed and in need of replacement.

Surgical Driver

Figure 1:
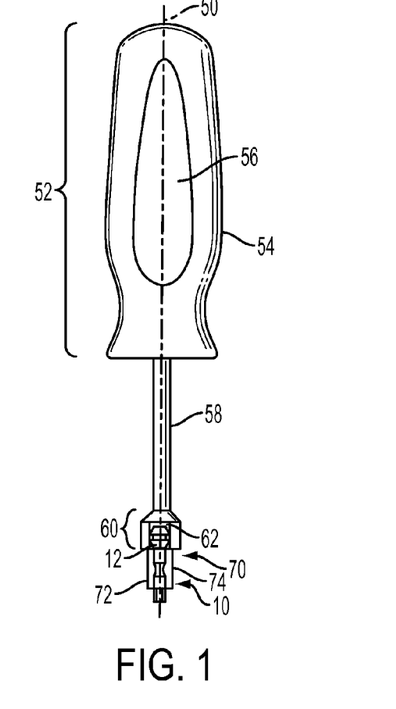
FIG. 1 is a partially transparent side view of one exemplary embodiment of a surgical driver having a modular driver tip with a containment shield disposed at least partially therearound.

FIG. 1 illustrates one exemplary embodiment of a surgical tool or driver 48 that includes a modular driver tip 10 having a containment shield 70 associated therewith. The driver 48 can be an elongate member having a longitudinal axis 50. A proximal portion 52 of the driver 48 can include a handle 54 with a gripping area 56. An elongate rod or shaft 58 can extend from the handle 54 and terminate in a distal, head end 60 of the driver 48. The distal end 60 can be configured to receive a modular driver tip. As shown, the distal end 60 includes a tip-receiving socket 62 within which a proximal region 12 of the modular driver tip 10 can be removably and replaceably mounted. While the driver tip 10 can be secured to the driver 48 using any number of techniques known to those skilled in the art, in the illustrated embodiment the proximal region 12 is securely held within the socket 62 by way of an interference fit that, at least up to the predetermined threshold torque value for a given driver tip, prevents rotation of the tip 10 independent of the driver 48. A holding force imparted by the socket 62 on the tip 10 for preventing rotation of the tip 10 independent of the driver 48 is generally greater than the threshold torque value. In some embodiments the holding force is greater than or equal to two times the threshold torque value. Further, a person skilled in the art will appreciate that the proximal portion 52 of the driver 48 may have other features, in addition to or instead of gripping area 56, or may have a different geometry to facilitate the gripping of the handle 54.

Modular Driver Tips

Modular driver tips for use in conjunction with surgical drivers such as the driver 48 can have a variety of different configurations. The tips are generally torque-limiting, meaning that once a threshold torque is applied to the tip, the tip deforms to prevent further torque from being applied to the driven member with which it is mated. This allows for a controlled and reliable torque to be applied to the driven member. A person skilled in the art will recognize a number of different types and configurations of tips that are torque-limiting, but in the embodiment of FIGS. 2A, 2B, and 2C, the tip 10 has a proximal region 12 that is adapted for mating within a driver and a distal region 14 that engages and applies torque to a driven member. An intermediate region 16 is disposed between the proximal and distal regions 12, 14 of the modular driver tip 10.

Figure 2A:
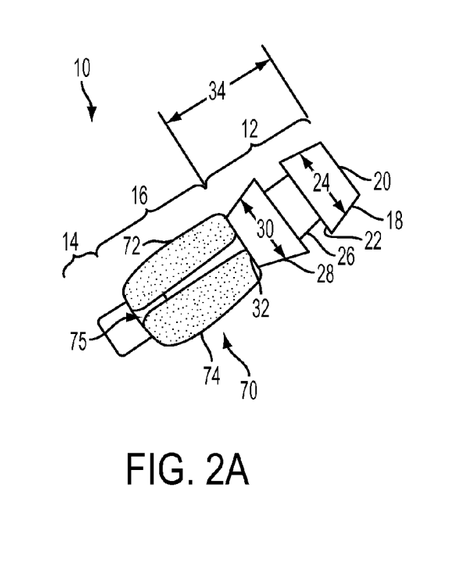
FIG. 2A is a schematic view of the modular driver tip and the containment shield of FIG. 1.

The proximal region 12 may be of virtually any size and shape that renders it suitable to be mated with a driver, such as by an interference fit. In the illustrated embodiment, the proximal region 12 includes a tapered first region 18 that extends from an end wall 20 to a shoulder 22. The first region 18 is tapered such that its diameter 24 decreases from a maximum adjacent the shoulder 22 to a minimum adjacent the end wall 20.

In one embodiment the proximal region 12 may also include an intermediate zone 26 distally adjacent to the shoulder 22 of the first tapered region 18, and a second tapered region 28 that is distally adjacent to the intermediate zone. The second tapered region 28 has a taper that is the reverse of that of the first region 18. That is, region 28 has a diameter 30 that tapers from a maximum adjacent the intermediate zone 26 to a minimum at a distal end 32 thereof.

A person skilled in the art will readily understand that the dimensions of the proximal region 12 may be varied depending upon the requirements of a given application of the tip 10 and driver. By way of example, however, the proximal region 12 may have a length 34 in the range of about 5 millimeters to about 15 millimeters. The diameter of regions 18 and 28 may taper from a maximum of about 10 millimeters to about 25 millimeters, to a minimum of about 2 millimeters to about 5 millimeters. Generally, the angle of taper is in the range of about 20 degrees to about 30 degrees. Each of regions 18 and 28 may have a length in the range of about 1 millimeter to about 6 millimeters.

The intermediate region 16 can be generally cylindrical and extend over a length of about 5 millimeters to about 25 millimeters. Intermediate region 16 can include a first cylindrical zone 36 and a second cylindrical zone 38. Optionally, a reduced diameter zone 40 may be disposed between zones 36 and 38. Where zone 40 is present, each of zones 36, 38, 40 may have a length in the range of about 2 millimeters to about 10 millimeters. Reduced diameter zone 40 can be useful to promote fracture or failure of the insert 10 within the reduced diameter zone when a predetermined minimum level of torque is achieved or exceeded.

Figure 2B:
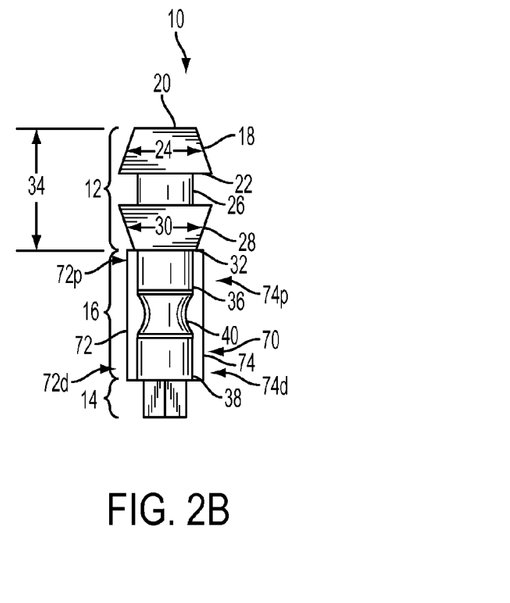
FIG. 2B is a plan view of the modular driver tip and the containment shield of FIG. 2A.
Figure 2C:
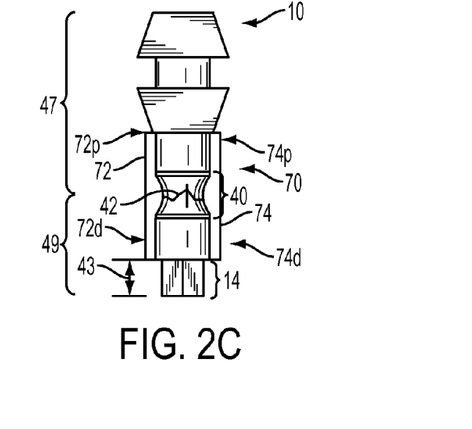
FIG. 2C is a plan view of the modular driver tip and the containment shield of FIG. 2A, the tip having a deformation formed therein.

FIG. 2C illustrates a possible mode of failure or deformation of the modular driver tip 10 in which a crack 42 has propagated across the reduced diameter zone 40. The formation of the crack 42 within the zone 40 would be noticeable either visually, and/or tactually, and/or aurally, or otherwise, and would prevent further application of torque to a driven member.

The tip 10 may be designed so as to provide indications of achieving or exceeding a predetermined level of torque (i.e., a threshold torque value) other than by fracture or failure in reduced diameter zone 40. For example, the distal region 14 of the tip 10 can be engineered to deform and roll over the driven member without applying additional torque, upon reaching a predetermined level of torque. Regardless of how the tip 10 fails to deliver further torque to a driven member, a person skilled in the art will understand that the insert is intended to be a disposable, single-use element. Examples and further details of driver tip members and related components that can be used in conjunction with the disclosures herein can be found in U.S. Pat. No. 6,308,598 entitled "Modular Torque-Limiting Driver System for Medical Applications," the content of which is incorporated by reference in its entirety.

A person skilled in the art will understand that the shape and dimensions of the tip 10 can be designed to promote failure at a certain torque level. Further, the choice of materials from which the tip 10 can be made also affects the predetermined minimum level of torque that can be applied by the insert. Also, the material selection is dependent upon several characteristics including, but not limited to, the desired threshold torque value and the technique used to sterilize the tip 10.

In the illustrated embodiment, the distal region 14 of the tip 10 is substantially hexagonal in shape, in the form of a male "hex head," and it is dimensioned to be inserted within a female hexagonal receptacle of a driven member. The distal region 14 can generally have a longitudinal length 43 in the range of about 1 millimeter to about 5 millimeters. A person skilled in the art will appreciate, however, that the distal region 14 may have another shape while still allowing the tip 10 to be effective to impart torque to a driven member.

The tip 10 can be made of a variety of materials known to be suitable for use with surgical devices, including polymers, ceramics, composites, and metals or metal alloys. Exemplary polymers include polypropylene, polyurethane, ultra-high molecular weight polyethylene, polyethylene, polysulfones, polycarbonates, polyamides, liquid crystal polymers, polyethersulfones, and polyphenylsulfones. Exemplary metals include cobalt, titanium, and aluminum, and exemplary metal alloys include 400 series stainless steel, cobalt alloys, aluminum alloys, and titanium alloys.

Containment Sheilds

As shown in FIGS. 2A-2C, disposed around at least a portion of the modular driver tips 10 can be a containment shield 70. The containment shield 70 can be associated with the surgical driver 48 to allow it to receive at least a portion of the tip 10 after it is deformed. In the illustrated embodiment the shield 70 includes two opposed plates 72, 74, each of which is coupled to an upper portion 47 (FIG. 2C) and a lower portion 49 (FIG. 2C) of the tip 10 to receive the upper and lower portions 47, 49 after the tip 10 has fractured into two pieces. The plates 72, 74 are generally cylindrical in nature in that they have a curved profile that substantially mimics the curve of the portion of the tip around which they are disposed. The plates 72, 74 also have proximal ends 72p, 74p and distal ends 72d, 74d that extend substantially transverse to the body of the plates 72, 74 so they can be mated to the tip 10. As shown, the proximal and distal ends 72p, 74p and 72d, 74d can be spaced a distance apart from each other, with the resulting space 75 (FIG. 2A) generally being small enough to minimize the risk of pieces of the deformed tip 10 from falling through the space 75. In the illustrated embodiment, the two plates 72, 74 generally form a tube having two longitudinal cut-outs (spaces 75) formed therein.

Together the plates 72, 74 retain the deformed tip 10 with respect to the shaft 58 of the driver 48, thereby preventing the deformed pieces from falling into the surgical site, or to another location of the body. After the modular driver tip 10 is deformed, the shield 70, and the pieces of the tip 10 it receives, can be removed from the surgical site. Once the deformed pieces are removed, a new driver tip can be associated with the surgical driver 48 for subsequent use. As explained below, tips having different threshold torque values and different configurations for use in various aspects of surgical procedures can be used interchangeably with the driver 48. Additionally, while previously a piece of the deformed tip 10 could remain in the driven member, thereby preventing a further torque from being applied to the driven member, by removing the pieces of the deformed tip 10, torque can be applied to the driven member by a second tip in the same manner the first tip applied torque to it. Likewise, any rough surfaces associated with pieces of the deformed tip 10 can be removed by the shield 70, making the location of the surgical site safer.

The containment shield 70 can be coupled to the tip 10 at any number of locations and in any number of ways known to those skilled in the art. As shown, the proximal ends 72p, 74p of the plates 72, 74 can be rigidly affixed to the tip 10 at the distal end 32 of the second tapered region 28 by a press fit, and distal ends 72d, 74d of the plates 72, 74 can be rigidly affixed to the tip 10 at the second cylindrical zone 38 by a press fit. In other embodiments the shield can be affixed to different portions of the tip 10, or in some instances, the shaft 58 of the driver 48, without losing the shield's ability to receive deformed portions of the tip 10. Likewise, other known techniques for coupling one component to another can be used to associate the shield 70 with the tip 10, including, by way of non-limiting examples, a snap fit or a threaded connection between the ends 72p, 72d, 74p, 74d of the plates 72, 74 and the tip 10, or by heat shrinking the ends 72p, 72d, 74p, 74d to the tip 10. In some instances, only the proximal ends 72p, 74p of the plates 72, 74 are coupled to the tip 10 or shaft 58 of the driver 48.

The shield 70 can also be configured to remain associated with the tip 10, and thus a shaft 58 to which the tip 10 is coupled, until after the threshold torque is applied to the tip 10 to deform the tip. As a result, to the extent the shield 70 is removably and replaceably coupled to at least one of the tip 10 and the shaft 58 of the surgical driver 48, the connection therebetween can generally be maintained until after the threshold torque is applied to the tip 10 to deform the tip. Likewise, the shield 70 can be configured to withstand a pullout force in the proximal direction applied to the driver 48 without fracturing or becoming detached from the driver 48 prior to deformation of the tip 10. In some embodiments, after the tip 10 has been deformed, the shield 70, and portions of the tip 10 received by the shield 70, can be configured to detach from the driver 48 at a particular threshold pullout force. The threshold pullout force is generally greater than the threshold torque value.

The tip 10, and/or the shield 70 associated therewith, can include a threshold torque value designation marker that indicates the threshold torque at which the modular driver tip 10 deforms. For example, a first tip and/or shield can include a first color (e.g., red) on it to signify a particular threshold torque value (e.g., 5 Newton-meters), while a second tip and/or shield can include a different color (e.g., blue) on it to signify a different particular threshold torque value (e.g., 10 Newton-meters). A group of color-coded distal modular tips can thus be provided, with each color representing a different threshold torque value, the threshold torque values increasing, for example, by about 5 Newton-meters per tip. A person skilled in the art will recognize that the values of the threshold torque values, and the differences in values between differently marked tips, can be quite diverse, and can be based, at least in part, on the desired procedure(s) in which the set of tips will be used. Other examples of threshold torque value designation markers beyond colors include, but are not limited to, written threshold values on the shields or tips, different surface textures formed on the shields and/or tips (e.g., having longitudinal ridges, raised dots, divots, etc.), and different shapes of the shields and/or tips (e.g., having a triangular cross section, a square cross section, a pentagonal cross section, etc.).

Figure 18A:
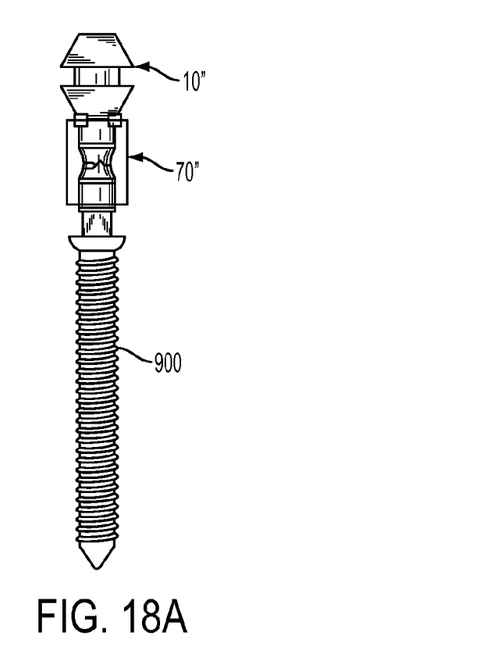
FIG. 18A is a plan view of the modular driver tip of FIG. 4A aligned for use with a long bone screw.
Figure 18B:
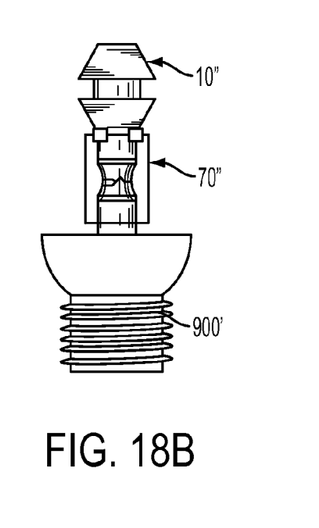
FIG. 18B is a plan view of the modular driver tip of FIG. 4A aligned for use with a hip or knee assembly screw.
Figure 18C:
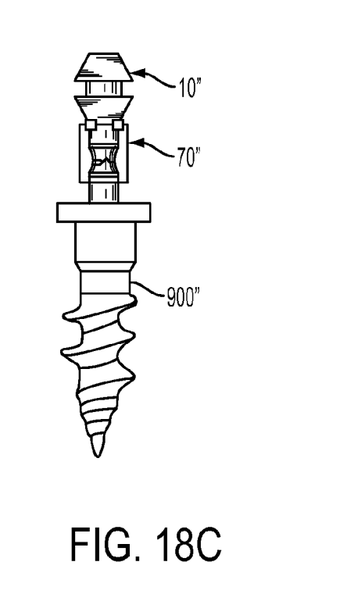
FIG. 18C is a plan view of the modular driver tip of FIG. 4A aligned for use with an arthroscopic fastener.

Similarly, tips and/or shields can have torque value designation markers to indicate other features of the tips. For example, the tips and/or shields can have torque value designation markers to indicate the type of driven member with which the tips should be used. By way of non-limiting example, a tip and shield configured for use with a long bone screw can be a different color than a tip and shield configured for use with a hip or knee assembly screw, which in turn can be a different color than a tip and shield configured for use with an arthroscopic fastener, examples of which are illustrated in FIGS. 18A, 18B, and 18C and described in greater detail below.

A person skilled in the art will readily understand that the overall construction of the shield 70, including its size and shape, and the materials used to create it, can depend on a variety of factors, including but not limited to the size, shape, and intended use of the other components with which it is used, the threshold torque values of the driver tip members, and the type of procedures with which the shield is to be used. The size and shape of the shield 70 is generally complementary to the size and shape of the driver tip 10 so that it can receive any deformed portions of the tip 10 that becomes separated from the driver after the threshold torque is applied. The cylindrically-shaped plates 72, 74 in the illustrated embodiment can each extend a length in the range of about 5 millimeters to about 25 millimeters, and the proximal ends 72p, 74p and distal ends 72d, 74d can each extend transversely from the bodies of the plates 72, 74 a length in the range of about 0.2 millimeters to about 5 millimeters. A width of the space 75 between the proximal and distal ends 72p, 72d of the plate 72 and the proximal and distal ends 74p, 74d of the plate 74 can generally be small enough to minimize the risk of pieces of the deformed tip 10 from falling therethrough. In one embodiment the width of the space 75 is in the range of about 0.5 millimeters to about 5 millimeters.

The shield 70 is typically configured such that it does not deform at torque levels at which its associated tip 10 deforms. In some embodiments, the shield 70 can have elastic properties, thereby allowing the shield 70 to be contorted when torque is applied to it without breaking. For example, the materials used to form the shield 70 can allow for the shield to be rotated up to approximately 270 degrees without breaking. Additionally, to the extent the tip 10 lengthens as a result of becoming deformed, for instance by separating into separate pieces, the elasticity of the shield 70 can allow the shield 70 to retain the deformed portions of the tip 10 without breaking. Materials used to form the shield 70 can include polymers, including polymers with elastomeric properties, composites, and metals or metal alloys, including but not limited to natural and synthetic rubbers, polyurethanes, silicones, vinyls, polyvinylidenes, polypropylenes, polyethylenes, polysulfones, polycarbonates, and polyamides. In one exemplary embodiment, the shield 70 is made from commercially pure titanium.

Alternative Configurations of Modular Driver Tips and Containment Shields

Figure 3A:
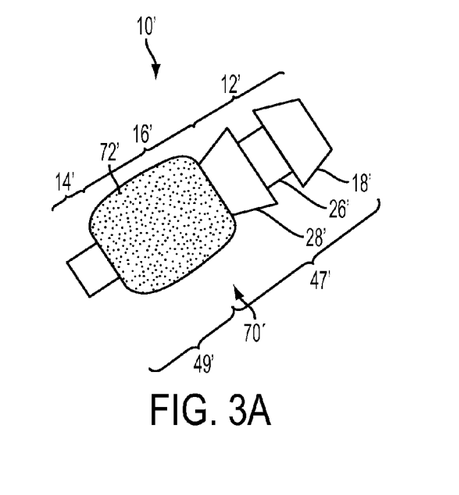
FIG. 3A is one exemplary embodiment of a modular driver tip and a containment shield disposed therearound.
Figure 3B:
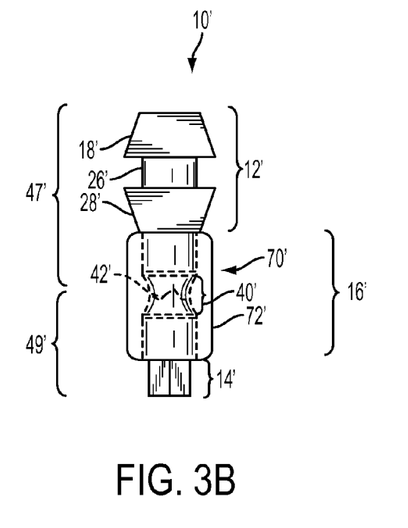
FIG. 3B is a plan view of the modular driver tip and the containment shield of FIG. 3A.

Further, while in the illustrated embodiment the shield 70 includes two plates 72, 74, the shield can also have a number of other configurations, including but not limited to three or more plates disposed around the tip, or a container or tube disposed substantially or completely around the tip. One such example of a shield 70' that is a container or tube 72' disposed around a tip 10' is illustrated in FIGS. 3A and 3B. As shown, the tip 10' has a proximal region 12' that is adapted for mating with a driver and a distal region 14' that engages and applies torque to a driven member. An intermediate region 16' is disposed between the proximal and distal regions 12', 14'. Similar to the tip 10 of FIGS. 2A-2C, the proximal region 12' can include first and second tapered regions 18', 28', with an intermediate zone 26' disposed therebetween. As shown, the tube 72' is coupled to both an upper portion 47' of the tip 10' and a lower portion 49' of the tip 10' such that it is completely disposed around at least a portion of the tip 10'. Accordingly, when the tip 10' is deformed, for instance by a fracture or crack 42' propagating across a reduced diameter zone 40' of the intermediate region 16' at a threshold torque, the container or tube 72' can retain the deformed portions of the tip 10' that separate themselves from the main portion of the driver.

The features and capabilities of the tube 72' are similar to as described with respect to the shield 70. A person skilled in the art would recognize how the various features and configurations of the shield 70 can be adapted to the tube 70'. Examples of the types of tubes that can be used as the shield 70' include a press fit sheath, a swaged tube, a heat shrink tube, and a metallic or polymeric tube or wrap. In one exemplary embodiment, the tube 72' is heat shrunk to the driver tip 10' at both the upper and lower portions 47', 49' of the tip 10'.

Figure 4A:
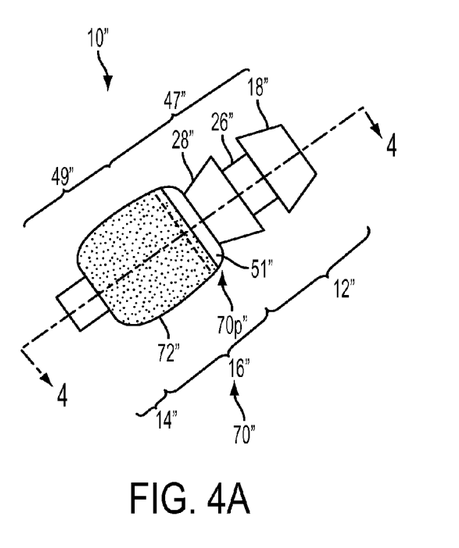
FIG. 4A is a schematic view of another exemplary embodiment of a modular driver tip having a containment shield disposed therearound and associated with a rotation track of the tip.
Figure 4B:
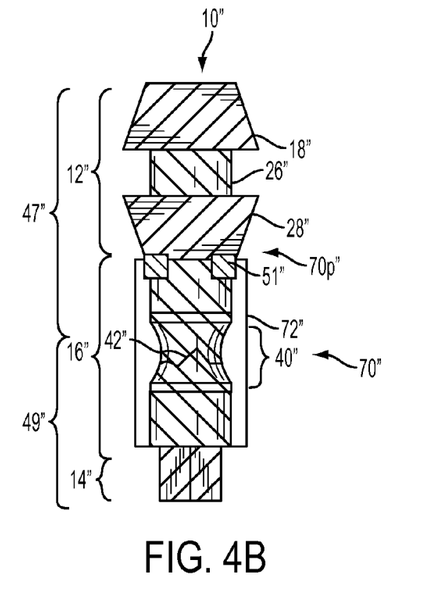
FIG. 4B is a cross-sectional view of the modular driver tip of FIG. 4A taken across the line 4-4.
Figure 4C:
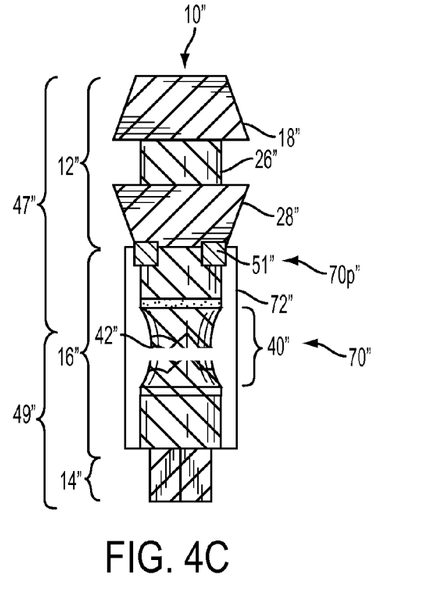
FIG. 4C is a cross-sectional view of the modular driver tip of FIG. 4A taken across the line 4-4 and having a deformation formed therein.

FIGS. 4A, 4B, and 4C illustrate another exemplary embodiment of a modular driver tip 10" having a containment shield 70" associated therewith. The tip 10" and shield 70" are generally constructed in a manner similar as described above with respect to the tip 10' and shield 70' of FIGS. 3A and 3B, and thus includes a shield 70" that is a container or tube 72" coupled to an upper portion 47" and a lower portion 49" of the tip 10", thereby completely disposing the tube 72" around at least a portion of the tip 10". Other similar components that are labeled in FIGS. 4A-4C include a proximal region 12" that is adapted for mating with a driver and having first and second tapered regions 18", 28" and an intermediate zone 26", a distal region 14" that engages and applies torque to a driven member, and an intermediate region 16" having a reduced diameter zone 40" across which a fracture or crack 42" can propagate once a threshold torque is achieved.

The shield 70" in FIGS. 4A-4C is different than the shields 70, 70' in previous embodiments in that it attaches to the upper portion 47" of the driver tip 10" in a different manner. As shown, a rotational track 51" is provided in the upper portion 47" and a proximal end 70p" of the shield 70" is disposed therein. The track 51" can extend around the circumference of the upper portion 47" of the tip 10", and the proximal end 70p" of the shield 70" can be sized and shaped to allow it to sit and move within the track 51". As a result, the shield 70" can rotate with respect to the driver tip 10", as well as with respect to a shaft of a driver with which the tip 10" is coupled. Further, as shown in FIG. 4C, the added flexibility associated with the connection between the shield 70" and the driver tip 10" can assist in allowing the shield 70" to expand after the threshold torque has been achieved and the lower portion 49" of the tip 10" breaks away from the upper portion 47". A person skilled in the art will recognize that other types of shields, such as the opposed plates 72, 74 of FIGS. 2A-2C, could also be disposed in the track 51" of the driver tip 10" without departing from the spirit of the invention. The plates 72, 74 could be allowed to move freely with respect to each other within the confines of the track 51", or alternatively, an attachment component could be disposed between and coupled to the plates 72, 74 to maintain the width of the space 75 therebetween.

Figure 5A:
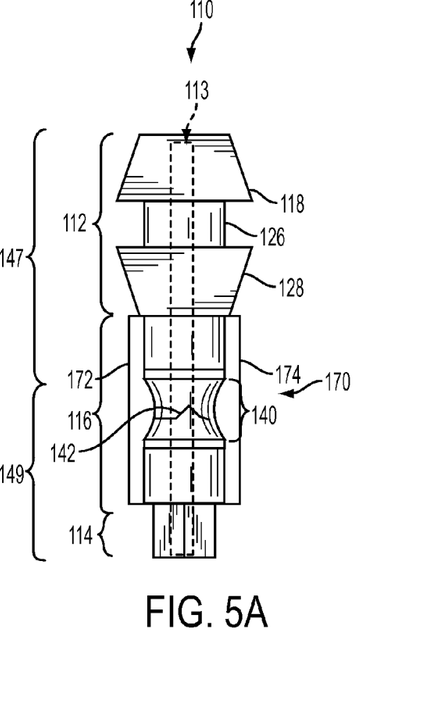
FIG. 5A is a plan view of yet another exemplary embodiment of a modular driver tip having a containment shield disposed at least partially therearound, the modular driver tip being cannulated.
Figure 5B:
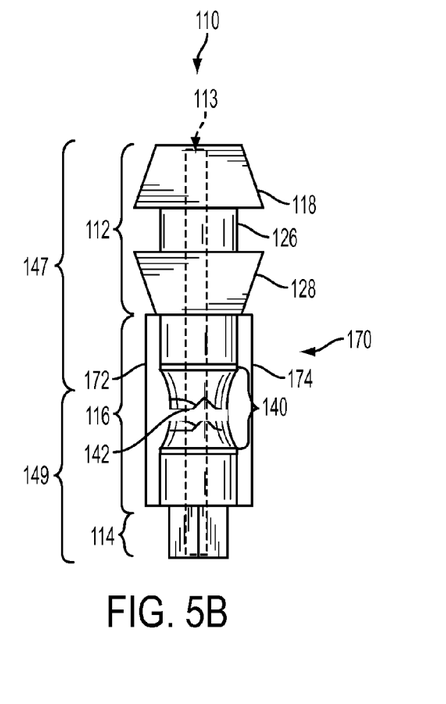
FIG. 5B is a plan view of the modular driver tip of FIG. 5A having a deformation formed therein.

FIGS. 5A and 5B illustrate still another exemplary embodiment of a modular driver tip 110 having a containment shield 170 associated therewith. The tip 110 and shield 170 are generally constructed and configured in a manner similar to as described with respect to FIGS. 2A-2C, with the tip 110 including a proximal region 112 that is adapted for mating with a driver and having first and second tapered regions 118, 128 and an intermediate zone 126, a distal region 114 that engages and applies torque to a driven member, and an intermediate region 116 having a reduced diameter zone 140 across which a fracture or crack 142 can propagate once a threshold torque is achieved. Additionally, the containment shield 170 can include plates 172, 174 mated at upper and lower portions 147, 149 of the tip 110, among other features. The tip 110 is different from the tip 10 of FIGS. 2A-2C in that the driver tip 110 is cannulated. As shown, a bore 113 extends through the entirety of the driver tip 110. The bore 113 can be any size, but is generally sized for use with a guide wire, as described in greater detail below with respect to FIG. 6. In one embodiment, the diameter of the bore 113 is in the range of about 0.2 millimeters to about 2 millimeters.

Surgical Systems

Figure 6:
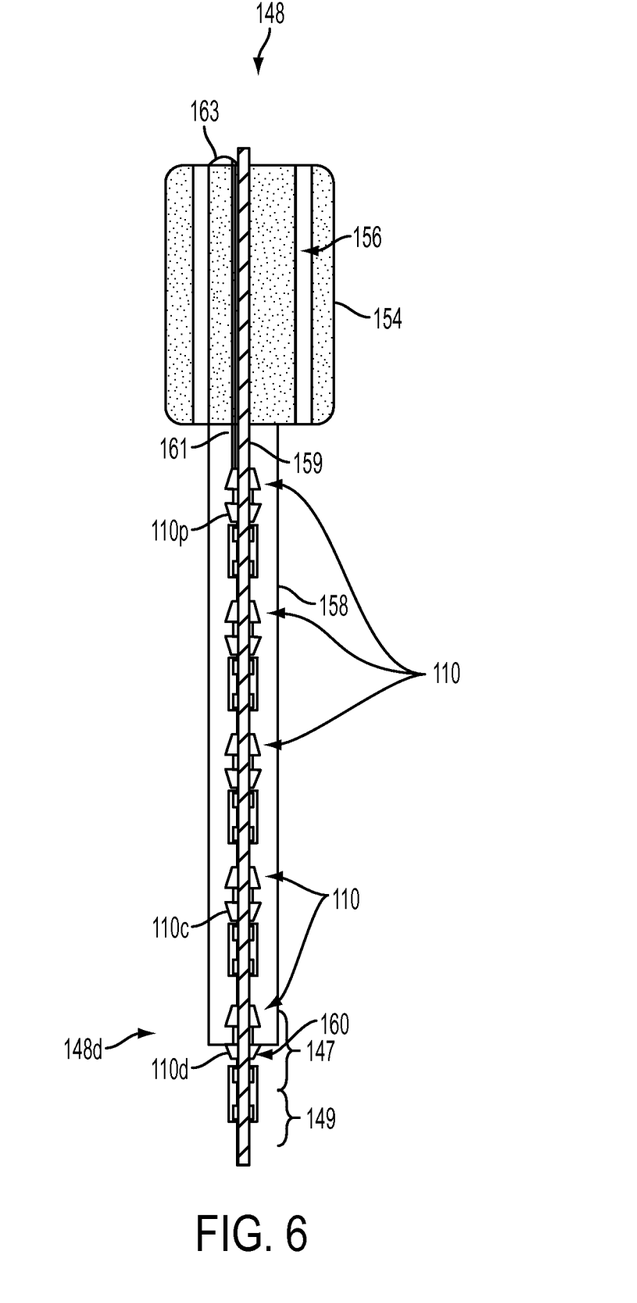
FIG. 6 is a partially transparent plan view of a surgical system having a plurality of the modular driver tips of FIG. 5A disposed within an interior volume of a cartridge and associated with a guide wire disposed through the cartridge.

While the modular tips and shields described herein can be used in conjunction with a driver 48 having a shaft 58 as described with respect to FIG. 1, in other embodiments the tips and shields can be used in conjunction with a surgical system having multiple tips ready for use. FIG. 6 illustrates one exemplary embodiment of a surgical system 148 having a handle 154, a cartridge 158 containing a plurality of modular driver tips disposed in an internal volume thereof, and a driver tip holder 160 disposed at a distal end 148d of the system 148. As shown, driver tips 110 of the type shown FIGS. 5A and 5B can be disposed within cartridge 158. The handle 154 can be configured to allow a user to supply torque to the distal-most driver tip 110d that is disposed in the driver tip holder 160. The cartridge 158 allows for a plurality of the modular driver tips 110 to be disposed in the system 148 for fast and convenient reloading of driver tips 110. This can improve the time it takes to perform procedures as torque can be applied to the driver tip 110 until it reaches its threshold torque value and deforms, at which point the driver tip 110 can be decoupled from the driver tip holder 160 and another driver tip 110 can be rapidly introduced into the driver tip holder 160 for subsequent use. The driver tip holder 160 can be configured to hold the distal-most driver tip 110d while torque is being applied thereto until the tip 110d deforms. Once the tip 110d deforms, the driver tip holder 160 can be configured to allow that tip to be removed from the holder 160 so that the next most-distal tip 110c can be seated in the driver tip holder 160 for use during a surgical procedure.

While a person skilled in the art will certainly recognize that the tips 110 can be moved distally through the cartridge 158 and to the driver tip holder 160 in a number of different manners, as shown an optional guide wire 159 that extends through the cartridge 158 and a pusher member 161 disposed proximal of the proximal-most tip 110p are adapted to move the tips 110 through the cartridge 158. The tips 110 can be disposed along the guide wire 159 and the pusher member 161 can apply a distal force to advance the tips 110 distally. The pusher member 161 can be associated with an actuation member, for example a trigger or button 163 disposed on the handle 154, such that each time the button 163 is depressed, the pusher member 161 supplies the distally directed force to distally advance the tips 110. The distal-most tip 110d, which is seated in the driver tip holder 160, can be pushed out of the holder 160, the tip 110c most proximal to the distal-most tip 110d can move into the driver tip holder 160, and the remaining driver tips 110 can advance distally. In one non-limiting alternative configuration, the button 163 can be pressed once to use a distal pusher member (not shown) to supply a force to the distal-most tip 110d that is sufficient to remove it from the driver tip holder 160 and a second time to use the proximal pusher member 161 to supply a force to the remaining tips 110 to advance them distally, with the now most distal tip 110c being seated in the driver tip holder 160. In a further non-limiting alternative configuration, two separate buttons can be used to operate proximal and distal pusher members. The distance and force supplied by one or more pusher members disposed in the cartridge 158 can be configured such that the driver tips 110 are not prematurely ejected from the driver tip holder 160.

The handle 154 of the system 148 can be configured in a variety of ways that allows a user to supply torque to the distal-most driver tip 110d disposed in the driver tip holder 160. In the system 148 of FIG. 6, the handle 154 is integrally formed with the cartridge 158 such that torque applied to the handle 154 is translated to the driver tip holder 160, and thus the tip 110d seated therein, thereby allowing the tip 110d to supply torque to a driven member to which the tip 110d is coupled. The handle 154 can include a gripping area 156 to allow for easy gripping of the system 148.

Figure 7:
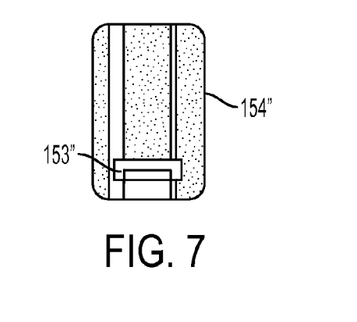
FIG. 7 is a partially transparent plan view of an exemplary embodiment of a handle of a surgical system.

In alternative embodiments the handle can be modular and thus cartridges can be selectively attached and detached from the handle. FIG. 7 illustrates one embodiment of a modular handle 154" including a mating feature 153" disposed therein that is complementary to a mating feature located on a proximal portion of a cartridge assembly. Any mating feature known to those skilled in the art can be used. For example, the mating feature 153" of the handle 154" can be a male coupling component and the mating feature of the cartridge assembly can be a female coupling component. Other examples of suitable mating features include, but are not limited to a Hudson adapter, a snap fit, and ball detents. In some embodiments, the modular handle 154" can be configured to rotate with respect to the cartridge, and thus the driver tip seated in the driver tip holder. A person skilled in the art will recognize a variety of configurations that can be used to allow a rotating handle to apply torque to the driver tip.

Figure 8:
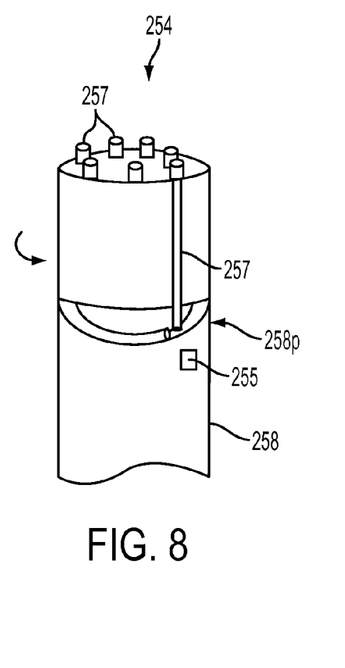
FIG. 8 is a partially transparent schematic view of an exemplary embodiment of a handle and a cartridge of a surgical system.
Figure 9:
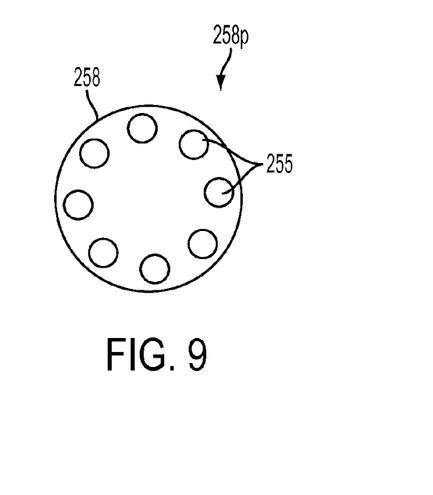
FIG. 9 is a top view of the cartridge of FIG. 8.

Still further, in some embodiments of a system, in lieu of or in addition to the driver tip deforming when a threshold torque value is reached, a handle can be configured to deform when a threshold torque value is reached. FIGS. 8 and 9 illustrate one such embodiment. As shown in FIG. 8, a handle 254 is configured to rotatably apply torque to a cartridge 258, and thus to a driver tip (not shown) associated therewith, until a threshold torque value is achieved. The handle can have a variety of shapes, but as shown it is generally cylindrical. Further, the handle can include a plurality of depressible keys 257 formed therein, and, as shown in FIG. 9, one or more bores 255 can be formed in a proximal portion 258p of the cartridge 258 that can be complementary to the keys 257. More particularly, each key 257 and each bore 255 can be configured to be associated with a threshold torque value. Once a threshold torque value is reached, the associated key 257 can become disposed in the associated bore 255 such that further torque will cause the key 257 to shear within the bore 255. Once the key 257 is sheared, the handle 254 can no longer apply torque to the cartridge 258 or the associated driver tip. A person skilled in the art will recognize a number of different ways by which a raised key 257 can be depressed into the respective bore 255, including by a user-supplied force, by spring-loading the keys 257, or by gravity. The threshold torque values associated with the keys 257 and bores 255 can generally be set by choosing particular diameters and cross-sectional areas of the keys 257 and bores 255. The keys 257 and bores 255s can be any number of shapes and sizes. In one exemplary embodiment, the keys 257 and bores 255 are generally cylindrical and have diameters and cross-sectional areas in the range of about 0.2 millimeters to about 5 millimeters. The type of and of material used to form the keys 257 and the proximal portion 258p of the cartridge 258 can also affect the threshold torque value. Examples of materials that can be used to form the keys 257 and the proximal portion 258p of the cartridge 258 include polymers, ceramics, composites, and metals or metal alloys. Exemplary polymers include polypropylene, polyurethane, ultra-high molecular weight polyethylene, polyethylene, polysulfones, polycarbonates, polyamides, liquid crystal polymers, polyethersulfones, and polyphenylsulfones. Exemplary metals include cobalt, titanium, and aluminum, and exemplary metal alloys include 400 series stainless steel, cobalt alloys, aluminum alloys, and titanium alloys.

Figure 10:
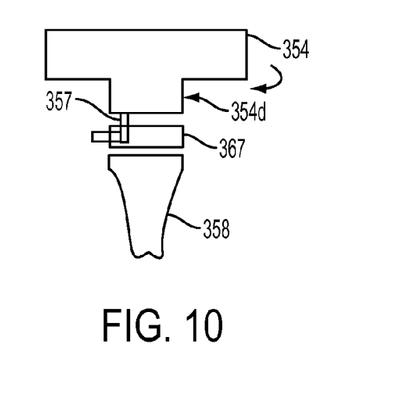
FIG. 10 is a partially transparent side view of an exemplary embodiment of a handle, shear ring, and a cartridge of a surgical system.
Figure 11:
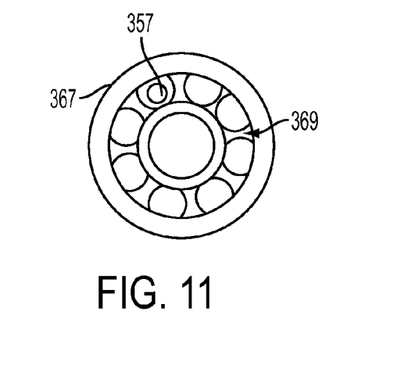
FIG. 11 is top view of the shear ring of FIG. 10.

FIGS. 10 and 11 illustrate another embodiment of a system in which a handle 354 is configured to deform when a threshold torque value is achieved in lieu of or in addition to the driver tip deforming. As shown in FIG. 10, the handle 354 can be configured to rotatably apply torque to a shear ring 367. The shear ring 367 can be coupled to the cartridge 358 to allow torque applied to the shear ring 367 to translate to the cartridge 358, and thus to a driver tip (not shown) associated therewith. This transfer of torque can continue until a threshold torque value is attained. The handle 354 can have a variety of shapes, but as shown it is generally T-shaped and includes a pin 357 at its distal end 354d. The pin 357 is configured to assist in supplying torque to the shear ring 367 until the pin 357 shears. More particularly, the pin 357 can be disposed in webbing 369 of the shear ring 367 and travel therethrough until the webbing 369 shears the pin 357 at the threshold torque value. The type of material and thickness or density of the webbing 369 can be used to set the threshold torque value. Once the pin 357 is sheared, the handle 354 can no longer apply torque to the shear ring 367, cartridge 358, or the associated driver tip. In exemplary embodiments, the webbing 369 can be made of polymers, ceramics, composites, and metals or metal alloys that are fabricated to have a desired breaking point and can have a density of about 1000 kg/m$^3$ to about 20,000 kg/m$^3$. Exemplary polymers include polypropylene, polyurethane, ultra-high molecular weight polyethylene, polyethylene, polysulfones, polycarbonates, polyamides, liquid crystal polymers, polyethersulfones, and polyphenylsulfones. Exemplary metals include cobalt, titanium, and aluminum, and exemplary metal alloys include 400 series stainless steel, cobalt alloys, aluminum alloys, and titanium alloys.

Cartridges

Cartridges having multiple tips disposed in a volume thereof can have a variety of configurations that allow for the tips to be moved to a driver tip holder and subsequently used to supply torque to a driven member. In FIG. 6 the cartridge 158 includes a guide wire 159, a pusher member 161, and a button 163 to distally advance the tips 110 through the cartridge 158 and into the driver tip holder 160. A person skilled in the art will recognize a number of other known techniques for advancing components such as the driver tips through a cartridge assembly. For example, the tips can be spring-loaded into the cartridge such that each time an actuation member on the handle is pressed, the springs eject the driver tip in the driver tip holder and advance the driver tip adjacent to the driver tip holder. Actuation members can include buttons, triggers, rotating dials, and other known ways to actuate a spring.

Figure 12A:
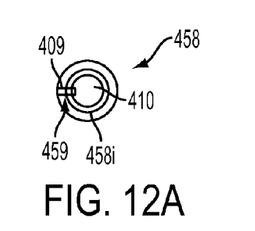
FIG. 12A is top view of one exemplary embodiment of a cartridge of a surgical system having an alignment feature disposed therein.
Figure 12B:
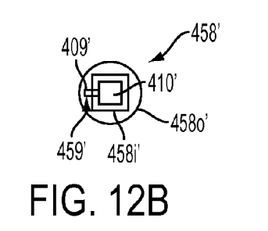
FIG. 12B is a top view of another exemplary embodiment of a cartridge of a surgical system having an alignment feature disposed therein.

FIGS. 12A and 12B illustrated two further examples of cartridge configurations that can be used to help advance a driver tip toward a driver tip holder. In some embodiments the driver tips can include a male or female mating component and the cartridge can include a complementary male or female mating component. As shown in FIG. 12A, the driver tip 410 is substantially cylindrical in shape and includes a male key member 409 located on one side thereof. The substantially cylindrically shaped cartridge 458, in turn, includes a groove 459 formed in an internal wall 458i that is complementary in shape to the male key member 409 of the driver tip 410. Each driver tip 410 disposed in the cartridge 458 can slide within the groove 459 of the inner wall 458i, thereby helping to keep the driver tips 410 aligned for eventual seating in a driver tip holder (not shown). The tips 410 can be advanced distally toward the driver tip holder by any techniques known to those skilled in the art, including but not limited to using any combination of pusher members, springs, and actuation members as described herein.

The cartridge 458' and tip 410' configuration of FIG. 12B is similar to that of FIG. 12A except that the driver tip 410' and an internal wall 458i' of the cartridge 458' are both substantially rectangular in shape. As shown, an outer wall 458o' of the cartridge 458 can be substantially cylindrical even though the inner wall 458i' is not, although they can both be rectangular or cylindrical in shape. A male key member 409' of the driver tip 410' can be complementary to a groove 459' formed in the internal wall 458i' of the cartridge 458', and the driver tips 410' can be advanced through the cartridge 458' and to the driver tip holder (not shown) in manners similar to the tips 410 of FIG. 12A. In alternative embodiments, the male key members 409, 409' can be formed on the internal walls 458i, 458i' and the groove 459, 459' can be formed in the driver tips 410, 410'.

Figure 13A:
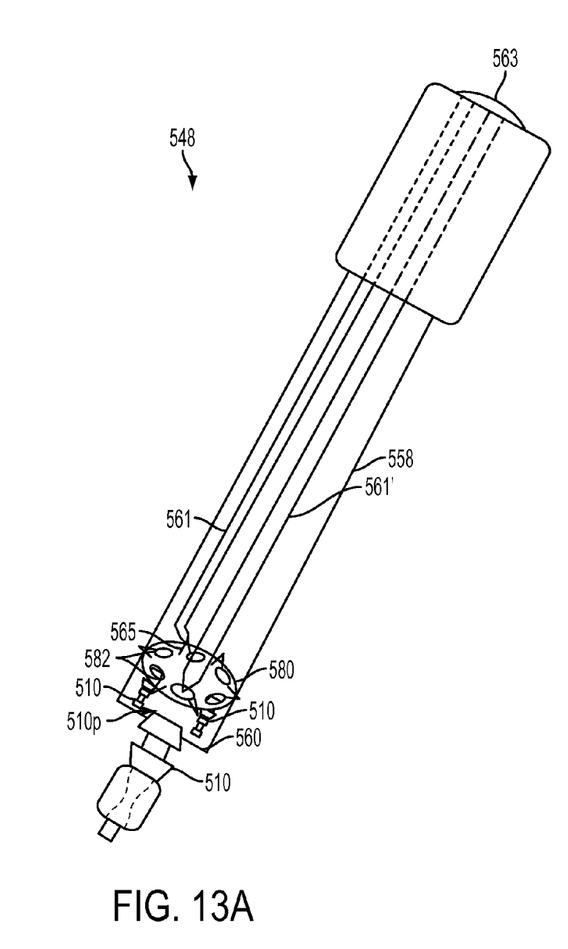
FIG. 13A is a schematic view of another exemplary embodiment of a surgical system having a plurality of modular driver tips and a rotatable, multiple chamber cylinder disposed within an interior volume of a cartridge.
Figure 13B:
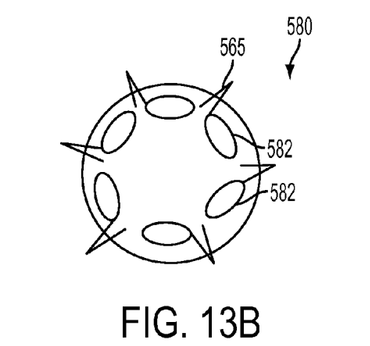
FIG. 13B is a schematic top view of the rotatable, multiple chamber cylinder of FIG. 13A.

FIGS. 13A and 13B illustrate a system 548 having an alternative configuration of a component for use in a cartridge 558 to allow multiple driver tips 510 to be supplied to a driver tip holder 560. The component includes a rotatable cylinder 580 having a plurality of chambers 582 disposed therein. Each chamber 582 can be configured to receive a driver tip 510 for storage thereof, and the cylinder 580 can be rotated such that one chamber 582 at a time is disposed adjacent to the driver tip holder 560. While the cylinder 580 can be rotated using any number of known techniques, in one embodiment the cylinder 580 includes one or more ratchets 565 and an actuation mechanism, such as a trigger or button 563, coupled to a pawl 561 such that pushing the button 563 causes the pawl 561 to engage a ratchet 565 to rotate the cylinder 580. Once a chamber 582 is in line with the driver holder 560, the driver tip 510 can be ejected from the chamber 582 and into the driver tip holder 560. Any known technique for moving the driver tip 510 from the chamber 582 to the driver tip holder 560 can be used, and in the illustrated embodiment the button 563 is also coupled to a spring-loaded hammer 561' that is configured to engage a proximal end of the tip 510 to push the tip 510 out of the chamber 582 and into the driver tip holder 560. In some embodiments, the system 548 can include visual (e.g., a light) and/or audio confirmation to a operator that the driver tip 510 is appropriately situated in the driver tip holder 560 because the driver tip holder 560 may be located at a surgical site and thus not visible to an operator Likewise, when the cartridge 558 contains no further driver tips 510, a different visual and/or audio confirmation can indicate to the operator that the cartridge 558 is empty.

A size and shape of cartridges of a system can depend, at least in part, on the size and shape of the other components of the system, the number and type of modular driver tips disposed therein, and the type of procedure with which the cartridge is being used. In the illustrated embodiments the cartridges are generally cylindrical in shape and have a longitudinal length in the range of about 100 millimeters to about 500 millimeters and a diameter in the range of about 1 millimeter to about 50 millimeters. A person skilled in the art will recognize a number of different materials that can be used to form the cartridge, including but not limited to polymers, ceramics, composites, and metals or metal alloys. Exemplary polymers include polypropylene, polyurethane, ultra-high molecular weight polyethylene, polyethylene, polysulfones, polyethersulfones, and polyphenylsulfones. Exemplary metals include cobalt, titanium, and aluminum, and exemplary metal alloys include 400 series stainless steel, cobalt alloys, aluminum alloys, and titanium alloys.

Driver Tip Holders

Turning back to FIG. 6, the driver tip holder 160 can be located distal of the handle 154 and can have a variety of configurations to hold a driver tip. As shown, the driver tip holder 160 is integrally formed with the cartridge 158, but in alternative embodiments it can be a separate component located distal of the handle 154 and the cartridge 158. Generally, the holding force applied by the driver tip holder 160 to the driver tip 110d seated therein is great enough to hold the tip 110d in place with respect to the cartridge 158 while a torque is applied to the tip 110d. For example, a holding force applied by the driver tip holder 160 to the driver tip 110d can be greater than or equal to two times the threshold torque value. Once a threshold torque value is reached and the tip 110d deforms, depending on how the tip deforms, the driver tip holder 160 may or may not retain the upper portion 147 of the driver tip 110. In one exemplary embodiment, the tip 110 deforms such that the upper portion 147 continues to be retained by the driver tip holder 160 after the threshold torque value is reached. In such an instance, a force can be applied to the driver tip 110d to remove it from the driver tip holder 160. The force can be applied in any number of manners, including by way of components such as the pusher member 161 disposed in the cartridge 158. When the driver tip 110d is ejected from the driver tip holder 160, the tip 110d can be removed from the surgical site. While the use of a containment shield in conjunction with tips 110 disposed in the cartridge 158 is optional, in embodiments in which the tips 110 include containment shields 170, the shield 170 can receive the deformed driver tip 110 and then the shield 170, and the portions of the tip 110 received by the shield 170, can be removed from the surgical site. Further, a size and shape of the driver tip holder can depend, at least in part, on the size and shape of the other components of the system, and in particular the size and shape of the cartridge and the modular driver tips configured to be disposed in the holder, the desired holding force of the driver tip holder, and the type of procedure with which the system is being used.

Figure 14:
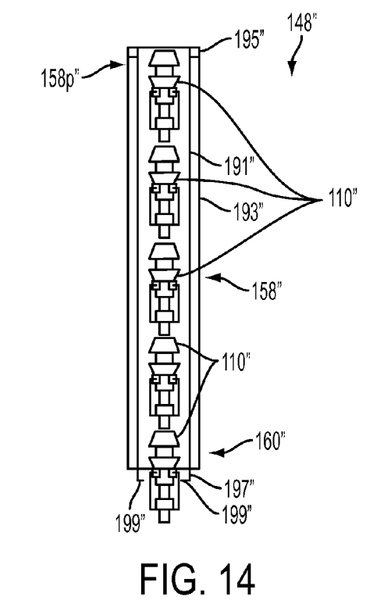
FIG. 14 is a partially transparent plan view of still another exemplary embodiment of a surgical system having a plurality of the modular driver tips of FIG. 4A disposed within an interior volume of a cartridge, the cartridge having an inner sleeve and an outer sleeve.

FIG. 14 illustrates one embodiment of a system 148" that has a driver tip holder 160" formed by an inner sleeve 191" of a cartridge 158". The inner sleeve 191" defines a volume of the cartridge 158" and a plurality of the modular driver tips 110" of FIGS. 4A-4C can be disposed therein. As shown, the inner sleeve 191" is at least partially disposed in an outer sleeve 193" of the cartridge 158", and relative motion of the sleeves 191" and 193" with respect to each other can advance and hold the driver tips 110" at a distal gripping portion 197" of the inner sleeve 191". For example, the outer sleeve 193" can be moved distally to constrain the distal gripping portion 197" of the inner sleeve 191" around the distal-most driver tip 110" to hold that tip for use in applying torque to a driven member. The outer sleeve 193" can then be moved proximally to release the distal-most driver tip 110" from the gripping portion 197", thereby allowing the next successive tip 110" to be advanced distally toward the gripping portion 197" so that the outer sleeve 193" can be advanced distally again to constrain the distal gripping portion 197" and thus hold the now distal-most driver tip 110" for use in applying torque to a driven member. A person skilled in the art will recognize that the inner sleeve 191" can also be advanced proximally and distally in a manner that allows the distal gripping portion 197" to be selectively constrained for purposes of holding and releasing driver tips 110", either in lieu of or in addition to movement of the outer sleeve 193". Further, at least a portion of the inner sleeve 191", for instance a portion that includes the distal gripping portion 197″, can be configured to be flexible to allow for flexing of the inner sleeve 191″ so that the driver tips 110″ can be selectively held and released.

As shown the distal gripping portion 197″ includes two walls 199″ that are substantially transverse to the walls of the inner sleeve 191″. The holding force supplied by the distal gripping portion 197″ is generally greater than the threshold torque value of any driver tip associated therewith, and in some embodiments the holding force is greater than or equal to two times the threshold torque value. Although no pusher or actuation members are illustrated, any number of techniques for advancing the tips 110″ through the volume of the cartridge 158″ can be used, including those techniques described herein. In the illustrated embodiment the outer sleeve 193″ includes a female mating component 195″ at a proximal portion 158p″ of the cartridge 158″ for mating with a handle, such as the handle 154″ of FIG. 7.

Use of the Surgical Drivers and Surgical Systems

In use, both the driver 48 and the systems, such as the systems 148, 148″, and 548, can apply torque to a driven member, such as a bone anchor or a fastening device. While the methods described herein are generally applicable to, and adaptable by a person skilled in the art for use with, all devices and systems disclosed herein and derivable therefrom, for convenience the method is described with respect to the system 148 illustrated in FIGS. 5A, 5B, and 6. If the cartridge 158 having driver tips 110 disposed therein is not already coupled or fixedly attached to a handle, it can be coupled to the handle 154 for supplying torque to a driven member. One of the driver tips 110, as shown tip 110d, can be seated in the driver tip holder 160 using techniques described above.

The tip 110 can then engage a fastener having a head with a receiving portion that is complementary to the distal end of the driver tip. Once the tip 110 is engaged with the fastener, an operator can apply torque to the driver by gripping and rotating the handle 148. The torque that results translates through the device, to the driver tip 110, and to the fastener. The operator can continue to apply torque to the system 148 until a threshold torque value is reached. Once the threshold torque value is reached, the driver tip 110 will deform, for instance by fracturing, and as a result any subsequent torque applied by the operator to the system 148 will not be effective to drive the fastener.

After the threshold torque value is attained, the driver tip 110 can be removed from the driver tip holder 160 by applying a force that is greater than the holding force of the holder 160 to the upper portion 147 of the tip 110. Any number of known ways for applying such a force can be used, including by manually pulling the tip 110 out of the holder 160 or by using the pusher member 161 or similar component to eject the driver tip 110 out of the holder 160. Once the tip 110 is decoupled from the device, the entire tip 110, as well as the shield 70, 170 associated therewith, can be removed as a single component because the shield 70, 170 maintains the approximate location of the deformed portions of the tip 10, 110 with respect to the driver 48 or system 148. A second tip can then be attached to the driver tip holder 60, 160 for use in applying torque to a driven member. With respect to the surgical driver 48, this can be done by manually introducing a second driver tip. With respect to the system 148, this can be done using any of the techniques described herein or known to those skilled in the art for advancing a driver tip 110 distally through the cartridge 158 and seating it in the driver tip holder 160. Because of the removable and replaceable nature of the driver tips 110, and further because different driver tips can be configured for different purposes and to have different threshold torque values, an operator can easily mix and match driver tips based on observed patient bone conditions and other conditions that may arise during the course of a procedure.

Additional Configurations

Figure 15:
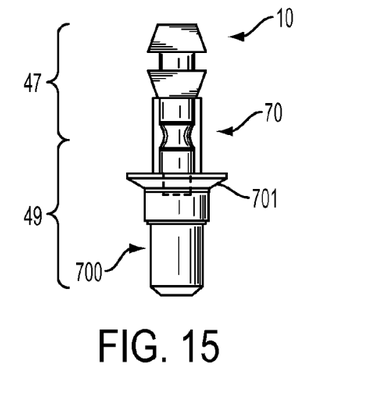
FIG. 15 is a plan view of the modular driver tip of FIG. 2A coupled to a driven member.

As shown in FIG. 15, in some embodiments the driver tip 10 of FIGS. 2A-2C can be pre-attached to a driven member 700. This can be advantageous, for example, when the driven member is small, and thus the operator does not have to engage the driver tip 10 with the driven member during surgery. It can also allow tips to be prepackaged in a sterile manner with the driven members. Once the tip and associated driven member are removed from the package, they can be easily positioned to allow a surgical driver to easily engage the tip, or an operator can easily hold the tip and associated driven member and couple it to the driver by hand. As shown, the containment shield 70 can be mated with the upper and lower portions 47, 49 of the driver tip 10, while the distal region 14 of the tip 10 is pre-attached to a receiving portion 701 of the driven member 700. In such instances, after the threshold torque value is attained, the driver tip 10 can be decoupled from the driven member 700. Thus, when the driver tip 10 and associated containment shield 70 are decoupled from the driver and removed from the surgical site, the driven member 700 can remain in its desired position. Tips having pre-attached driven members can also be disposed within cartridges of surgical systems like the cartridges described herein.

Figure 16:
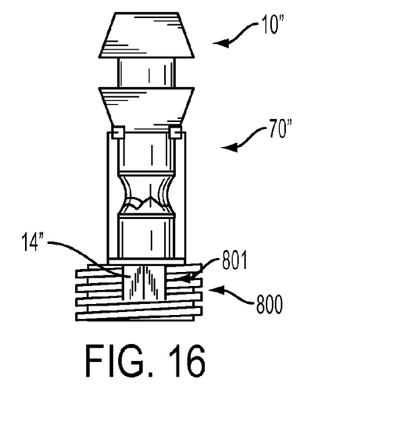
FIG. 16 is a plan view of the modular driver tip of FIG. 4A coupled to a driven member.
Figure 17A:
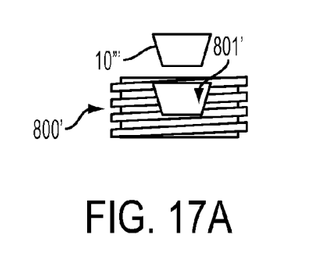
FIG. 17A is a cross-sectional view of one exemplary embodiment of a distal end of a modular driver tip and a complementary receiving end of a driven member.
Figure 17B:
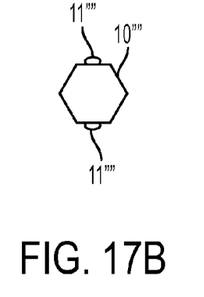
FIG. 17B is a bottom view of another exemplary embodiment of a distal end of a modular driver tip having compressible ribs or springs.
Figure 17C:
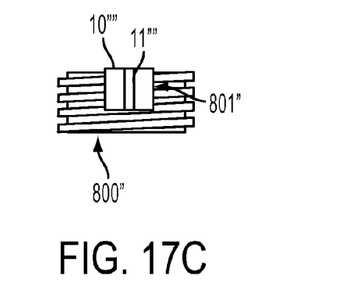
FIG. 17C is a cross-sectional view of the modular driver tip of FIG. 17B disposed in a bore of a driven member.
Figure 17D:
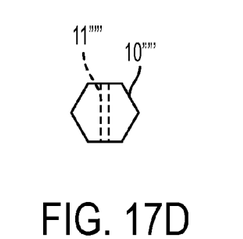
FIG. 17D is a bottom view of yet another exemplary embodiment of a distal end of a modular driver tip having a flexion slot.
Figure 17E:
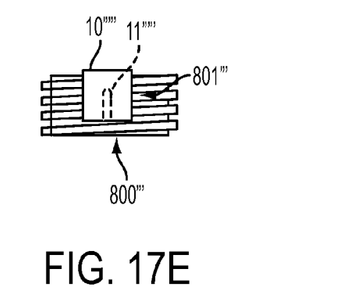
FIG. 17E is a cross-sectional view of the modular driver tip of FIG. 17D disposed in a bore of a driven member.

FIG. 16 illustrates another embodiment in which the driver tip 10″ and the associated containment shield 70″ of FIGS. 4A-4C are pre-attached to a driven member 800, such as a set screw. As shown, the distal region 14″ of the driver tip 10″ is press fit into a bore 801 of the driven member 800. Other configurations for coupling a driver tip to a driven member can also be used, including, by way of non-limiting examples, the coupling configurations illustrated in FIGS. 17A-17E. As shown in FIG. 17A, the driver tip 10′″ can have a tapered distal end and a bore 801′ of the driven member 800′ can have a complementary taper such that together they form a taper lock. As shown in FIGS. 17B and 17C, the driver tip 10″″ can include one or more compressible ribs or springs 11″″ and a bore 801″ of the driven member 800″ can be shaped such that when the tip 10″″ is compressed therein, a press fit lock is formed by the compressible ribs or springs 11″″. As shown in FIGS. 17D and 17E, the driver tip 11″″′ can include one or more flexion slots 11″″′ and a bore 801′″ of the driven member 800′″ can be shaped such that when the tip 10″″′ is compressed therein, a press fit lock is formed by the flexion slot 11″″′.

As described above, the driver tips can be configured for use with a number of different types of procedures and driven members. For example, the tools and systems can be adapted for use in procedures involving the knee, hip, spine, as well as in association with neuro and trauma-type procedures. FIGS. 18A, 18B, and 18C illustrate three non-limiting examples of the types of driven members with which the driver tips and containment shields can be used. As shown in FIG. 18A, the driver tip 10″ and associated containment shield 70″ of FIGS. 4A-4C can be coupled to a long bone screw 900, for example to insert the screw 900 into a femur. As shown in FIG. 18B, the driver tip 10″ and associated containment shield 70″ can be coupled to a smaller screw 900′. As shown in FIG. 18C, the driver tip 10″ and associated containment shield 70″ can be coupled to an arthroscopic fastener 900″.

The various tools and systems described herein can be packaged and sold as kit. For example, a surgical driver kit can include one or more handles, one or more shafts either removably or fixedly attached to the handles and having a tip driver holder at a distal end thereof, and a plurality of driver tips. The tips can all be configured for a similar use, or they can be configured for different uses as described herein. In exemplary embodiments the tips can be color-coded, for instance to designate different threshold torque values. The tips can include containment shields having any of the various configurations described herein. Optionally, driven members can be included as part of the kit, either as separate components or pre-attached to the driver tips Likewise, a surgical system kit can include one or more handles, one or more cartridges having a plurality of driver tips disposed therein, the cartridges being either removably or fixedly attached to the handles, and a tip driver holder disposed at a distal end of the cartridge. Similar to the color-coded tips, the cartridges can have threshold designation markers, such as being color-coded, to indicate the threshold values of the tips disposed therein. The tips within the cartridges can include containment shields having any of the various configurations described herein. Additionally, driven members can be included, either as separate components or pre-attached to the driver tips disposed in the cartridge.

A person skilled in the art will appreciate further features and advantages of the invention based on the above-described embodiments. The invention is not to be limited by what has been particularly shown and described, except as indicated by the appended claims. Accordingly, to the extent components and features are described with respect to a driver or a system, a person skilled in the art would understand how to adapt these components and features across the various configurations and embodiments provided herein. By way of non-limiting example, the torque-limiting handles 254, 354 of FIGS. 8-11 described with respect to systems and cartridges can be adapted by a person skilled in the art for use with the driver 48 and shaft 58 of FIG. 1. Likewise, any of the tips and shields described herein can be adapted for use in conjunction with any of the drivers, systems, handles, cartridges, and driver tip holders disclosed herein or otherwise known to those skilled in the art. All publications and references cited herein are expressly incorporated herein by reference in their entirety.

What is claimed is:

1. A tool, comprising:
   a driver having a proximal handle, a distal end, and a shaft disposed therebetween;
   a modular driver tip having a proximal end that is removably and replaceably matable to the distal end of the driver and a distal end that is configured to apply torque from the driver to a driven member, the tip being configured to deform at a threshold torque applied by the driver; and
   a containment shield disposed around at least a portion of the modular driver tip to receive at least a portion of the modular driver tip after deformation.

2. The tool of claim 1, wherein the tip is configured to break into two or more pieces.

3. The tool of claim 1, wherein the containment shield is configured to be removable from a surgical site with the at least a portion of the modular driver tip associated therewith.

4. The tool of claim 1, wherein the containment shield is press fit around at least a portion of the modular driver tip.

5. The tool of claim 1, wherein the containment shield is heat shrunk around at least a portion of the modular driver tip.

6. The tool of claim 1, wherein the containment shield comprises a container configured to retain the at least a portion of the modular driver tip after deformation thereof.

7. The tool of claim 1, wherein the containment shield is fixedly coupled to at least one of a proximal portion and a distal portion of the modular driver tip.

8. The tool of claim 1, wherein the containment shield is freely rotatable with respect to the shaft of the driver.

9. The tool of claim 1, wherein the modular driver tip comprises a plurality of modular driver tips, each having a proximal end that is removably and replaceably matable to the distal end of the driver and a distal end that is configured to apply torque from the driver to a driven member, each tip being configured to deform at a threshold toque value applied by the driver and each tip having a containment shield disposed around at least a portion thereof to receive at least a portion of the respective modular driver tip after deformation,
   wherein each modular driver tip of the plurality of modular driver tips includes a threshold designation marker indicative of the threshold torque at which the modular driver tip deforms.

10. The tool of claim 9, wherein the threshold designation marker is a color.

11. The tool of claim 1, wherein the shaft includes a cartridge assembly.

* * * * *